United States Patent [19]

Farrar et al.

[11] 3,939,198

[45] Feb. 17, 1976

[54] CHLORINATED NAPHTHALENE ESTERS

[75] Inventors: Grover L. Farrar, Westfield, N.J.; Phillip W. Storms, Dickinson, Tex.

[73] Assignee: Marathon Oil Company, Findlay, Ohio

[22] Filed: May 6, 1970

[21] Appl. No.: 35,244

Related U.S. Application Data

[63] Continuation-in-part of Ser. No. 529,221, Feb. 23, 1966, abandoned.

[52] U.S. Cl. ............ 260/469; 260/475 FR; 424/308
[51] Int. Cl.$^2$ ..................................... C07C 69/76
[58] Field of Search ............... 260/475, 475 FR, 469

[56] References Cited

UNITED STATES PATENTS

| | | | |
|---|---|---|---|
| 2,954,409 | 9/1960 | Swakon et al. | 260/650 |
| 3,194,794 | 7/1965 | Caldwell et al. | 260/78 |
| 3,255,235 | 6/1966 | Coran et al. | 260/475 FR |
| 3,426,035 | 2/1969 | Bremmer | 260/469 |

FOREIGN PATENTS OR APPLICATIONS

| | | | |
|---|---|---|---|
| 917,571 | 2/1963 | United Kingdom | 260/515 |

OTHER PUBLICATIONS

Price et al., J. Org. Chem. 14, 115–116 (1949).

*Primary Examiner*—Lorraine A. Weinberger
*Assistant Examiner*—Jane S. Myers
*Attorney, Agent, or Firm*—Joseph C. Herring; Jack L. Hummel

[57] ABSTRACT

A direct, essentially one-step method of preparing nuclearly chlorinated naphthalene esters which comprises forming a reaction mixture consisting essentially of a mono- or dicarboalkoxy substituted naphthalene, a chlorinated organic solvent having from 1 to 4 carbon atoms and a chlorination catalyst, heating the reaction mixture, and passing molecular chlorine into the mixture. The extent of the chlorination of the naphthalene mono- or diester can be controlled by varying the solvent employed, the amount of chlorine added and the reaction time. A number of unreported polychlorinated naphthalene esters and an acid chloride are obtained directly by the method. The esters can be used in the production of coloring materials, plastics and insecticides.

8 Claims, No Drawings

CHLORINATED NAPHTHALENE ESTERS

This application is a continuation-in-part application of application Ser. No. 529,221, filed February 23, 1966, now abandoned.

The present invention relates to a method of preparing chlorinated naphthalenes, particularly nuclearly chlorinated mono- and dicarboalkoxy substituted naphthalenes, and to products obtained thereby.

The direct nuclear halogenation of substituted naphthalenes has been recognized as being difficult or impossible due, in the main, to the blocking action of the substituents on the aromatic nucleus. British Pat. No. 917,571 mentions the problem, and proposes a method of halogenating substituted naphthalenes which involves reacting an aromatic compound with nitric acid of at least 40% concentration, and hydrochloric or hydrobromic acid and/or a metal halide. The aromatic compound used as a starting material in the method of the patent is characterized in that it is substituted in the aromatic nucleus by at least one carboxyl group or a group convertible to a carboxyl group by reaction of the compound with nitric acid, and, in cases where the nucleus is benzene the nucleus is further substituted by at least one alkyl or cyclohexyl group. The products obtained by the method are acid chlorides. In British Pat. No. 839,302, a method of preparing nuclear chloro-substituted aromatic carboxylic acid chlorides, also is disclosed. The method of that patent includes a first stage wherein an ester of an aromatic mono- or polycarboxylic acid is chlorinated with chlorine while exposed to light at a temperature above 100°C to produce the corresponding mono- or polycarboxylic acid chloride. A chlorination catalyst is then added to the reaction mixture, and the chlorination is continued in a second stage to produce the nuclear chloro-substituted aromatic carboxylic acid chloride. There is no teaching in British Pat. No. 893,302 with respect to the use of naphthalene esters as starting materials, nor, as in the case of British Pat. No. 917,571, is there any suggestion in the patent with respect to a method of directly chlorinating the aromatic nucleus of such esters to obtain, as an end product, the corresponding nuclearly chlorinated naphthalene ester. So far as is known, no method heretofore has been proposed for achieving such a result.

In accordance with the present invention there is provided an essentially one-step, efficient, inexpensive and direct method of preparing nuclearly chlorinated naphthalene esters in quantitative yields. The method not only is unique with respect to the ease with which it enables chlorination of such naphthalenes to be achieved, but also with respect to the facility with which it enables selective chlorination of the naphthalene esters to be attained. The method further has provided a route to a number of heretofore unreported nuclearly polychlorinated naphthalene esters, and an acid chloride.

Briefly, the method of the present invention includes the steps of forming a reaction mixture comprising a naphthalene mono- or diester, a $C_1$ to $C_4$ chlorinated organic solvent and an effective chlorination catalyst, heating the reaction mixture, and passing molecular chlorine into the mixture. The extent of the chlorination of the naphthalene ester effectively can be controlled by varying, among other things, the solvent employed, the amount of chlorine added to the reaction mixture and the reaction time. Generally speaking, the longer the reaction time, the more complete will be the chlorine substitution, even to the extent, in certain instances, of leading to chlorination of the ester substituent. The position of the ester substituent, or substituents, on the naphthalene nucleus does not appear to impede direct chlorine substitution at the unoccupied positions of the nucleus, and thus, quantitative yields of nuclearly chlorinated naphthalene esters can be obtained by the method of this invention whether there is an ester substituent on one or the other, or both, of the rings of the naphthalene ester.

The chlorinated organic solvents having utility for the purposes of this invention can be selected from a wide group. Exemplary thereof are chloroform, carbon tetrachloride, dichloroethylene, tetrachloroethylene, dichloroethane, 1,1,1-trichloroethane, n-propyl chloride, 1,1-dichloropropane, 2,2-dichloropropane, 1,1,2-trichloropropane, 1,2,3-trichloropropane, 1,1,3-trichloropropane, 1,1,1,2-tetrachloropropane, 1,1,2,2-tetrachloropropane, 1,2,2,3-tetrachloropropane, 1,1,2,3,3-pentachloropropane, 1,2,3-trichloropropene-1, n-butyl chloride, isobutyl chloride, t-butyl chloride, 2-chlorobutene-1, 1,2,3-trichlorobutane, 2,2,3-trichlorobutane, and compatible mixtures of any two or more thereof. As indicated, the chlorinated solvent utilized in the practice of the method of this invention is a factor in controlling the extent to which direct chlorine substitution on the naphthalene nucleus occurs. Thus, by way of illustration, when using tetrachloroethylene as the solvent, a tetrachloro-, pentachloro-, or a hexachloro-naphthalene mono- or diester can be prepared depending upon the reaction time. Using carbon tetrachloride as the solvent, on the other hand, nuclearly substituted mono- and dichloro- products can be obtained.

The nature of the products produced with the chlorinated solvent is related to the temperature of the reaction mixture and to the solubility of the reactants and products in the solvent. In those instances, for example, where it is desired to effect direct chlorine substitution at four, or more positions on the naphthalene nucleus, a solvent having a boiling point which will result in a reaction mixture having a reflux temperature greater than about 110°C should be used. Thus, in the foregoing specific illustrations, tetrachloroethylene, which has a boiling point of about 121°C, provides a reaction mixture having a reflux temperature of the desired magnitude and good solubility properties for the reactants and products and, therefore, enables the preparation of tetra- or higher chlorine substituted products. In contrast thereto, carbon tetrachloride, which has a boiling point of only about 76.8°C and poor solubility properties with respect to the reactants and products, provides a reaction mixture with a reflux temperature below the stated level and, therefore, results in the production of mono- and dichloro- products, other conditions being equal.

Reaction temperatures are not narrowly critical and will depend, in the main, on the considerations just mentioned. Generally speaking, temperatures employed in the method will range from about 50°C to about 150°C, usually about 75°C to about 130°C, with a temperature range of about 110°C to about 120°C being preferred.

The quantity of chlorinated organic solvent utilized in forming the reaction mixture in accordance with the practice of the present invention can be varied within appreciable limits. The generally optimum objectives of the invention can be attained with proportions, basis parts by weight, of solvent to naphthalene ester of the order of about 20:1 to about 40:1, usually about 25 to 30 parts of the solvent to about 1 part of the ester.

The chlorination reaction, as indicated, advantageously is carried out in the presence of a chlorination catalyst. Exemplary of catalysts having utility for this purpose are Lewis acids such as ferric chloride, aluminum chloride, boron fluoride, and the like, or metallic iron in particulate form. Of this group, ferric chloride is preferred.

The amount of catalyst employed is variable. Generally speaking, the proportions, basis parts by weight, of catalyst to naphthalene ester will range from about 1 part of the catalyst to about 5 to about 80, usually about 10 to about 25, parts of the naphthalene ester.

As stated, the method of the present invention has provided a route to a number of heretofore unreported nuclearly polychlorinated naphthalene mono- and diesters, in addition to an acid chloride. The mono- and diesters can be used as pesticides, or they can be converted, as by saponification, to the corresponding chlorinated naphthalene acids to be used as coloring materials in the same manner as suggested for the products produced by the method of British Pat. No. 917,571. In addition, they can be used as polymer intermediates to produce, in combination with ethylene glycol, for example, solid, plastic-like materials of relatively high melting point having excellent flame retardant and electrical insulative properties. Illustrative of one group of new compounds produced in accordance with the practice of this invention are 1,4-dichloro-, 1,4,7,8-tetrachloro-, 1,3,4,7,8-pentachloro- and 1,3,4,5,7,8-hexachloro-2,6-dicarbomethoxynaphthalene from the chlorination of 2,6-dicarbomethoxynaphthalene. A similar group of polychlorinated compounds results from the chlorination of 2,7-dicarbomethoxynaphthalene, 1,5-dicarbomethoxynaphthalene and 1,8-dicarbomethoxynaphthalene.

Other new compounds prepared by the method of the present invention are those obtained by the chlorination of alpha- and beta-methyl naphthoates. By way of example, chlorination of alpha-methyl naphthoate has led to 3,4,5,7-tetrachloro-alpha-methyl naphthoate and, unexpectedly, to heptachloro-alpha-naphthalene carbonyl chloride. The latter compound is interesting in that it demonstrates the strong propensity of the method of this invention to favor chlorine substitution on the naphthalene nucleus in preference to chlorine attack on the ester substituent. It is also interesting that only substitution on the ring and no addition of chlorine to the ring is observed.

In order that the full details of the present invention may be better understood, the following examples are provided. These examples are merely illustrative of the practice of the method of the invention and it should be understood that they are not in any way to be construed as limitative of the full scope of the invention.

EXAMPLE 1

To a 1-liter stirred reactor are added 24.4 parts of 2,6-dicarbomethoxynaphthalene, 489 parts of tetrachloroethylene and 1 part each of metallic iron and anhydrous ferric chloride. The reaction mixture thus formed is brought to reflux and chlorine is bubbled through the mixture for 7 hours. The reaction mixture is then quenched with an acetone-chloroform mixture, washed with water and filtered to remove catalyst. The solvent is stripped on a flash evaporator. The residue is crystallized by treatment with methanol to give 28.3 parts of 1,4,7,8-tetrachloro-2,6-dicarbomethoxynaphthalene in the form of a white crystalline solid. The product, after recrystallization from a chloroform-methanol mixture, melts at 140°–141.5°C.

EXAMPLE 2

The procedure outlined in Example 1 is followed except that the reaction is carried out for an additional 3 hours. The product is 1,3,4,7,8-pentachloro-2,6-dicarbomethoxynaphthalene.

EXAMPLE 3

The procedure outlined in Example 1 is followed except that the reaction is carried out for 22 hours. The product is 1,3,4,5,7,8-hexachloro-2,6-dicarbomethoxynaphthalene.

EXAMPLE 4

To a 3-liter stirred reactor are added 146.4 parts of 2,6-dicarbomethoxynaphthalene, 2900 parts of tetrachloroethylene, and 2 parts each of metallic iron and anhydrous ferric chloride. The reaction mixture is brought to reflux and chlorine is bubbled through the mixture for 41 hours. Thereafter, the mixture is steam distilled to remove solvent and the solid residue (288.9 parts) is collected by filtration. The solid is crystallized from a chloroform-methanol solution to give hexachloro-2,6-naphthalene dicarbonyl chloride.

EXAMPLE 5

To a 1-liter stirred reactor are added 24.4 parts of 2,6-dicarbomethoxynaphthalene, 475 parts of carbon tetrachloride, and 1 part each of metallic iron and ferric chloride. The reaction mixture is brought to reflux and treated with chlorine for 5 hours. The solvent is stripped and the residue crystallized from benzene to give a mixture of 4-chloro- and 1,4-dichloro-2,dicarbomethoxy-naphthalene.

EXAMPLE 6

The procedure outlined in Example 5 is followed except that 1,2,3-trichloropropane is used as the solvent and aluminum chloride is used as the catalyst. The products are a mixture of 4-chloro- and 1,4-dichloro-2,6-dicarbomethoxynaphthalene.

EXAMPLE 7

To a 500 milliliter stirred reactor are added 10 parts of alpha-methyl naphthoate, 325 parts of tetrachloroethylene, 1 part of metallic iron and 1.5 parts of ferric chloride. The reaction is brought to reflux and chlorinated for 4 hours by bubbling molecular chlorine through the reaction mixture. After steam distillation, the oily product is saponified to give 11 parts of 3,4,5,7-tetrachloro-alpha-naphthoic acid.

EXAMPLE 8

The procedure of Example 7 is followed except that chlorine is bubbled through the reaction mixture for 8 hours. The product is 2,3,4,6,7,8-hexachloro-alpha-methyl naphthoate.

EXAMPLE 9

To a 500 milliliter stirred reactor are added 10 parts of alpha-methyl naphthoate, 325 parts tetrachloroethylene, and 1 part each of metallic iron and ferric chloride. The reaction mixture is brought to reflux and chlorinated for 18 hours. After steam distillation, the crude solid product (23.4 parts) is separated by filtration. Yellow needles (M.P. 163°–165°C) of heptachloro-alpha-naphthoyl chloride are obtained on recrystallization from tetrachloroethylene. The acyl halide is hydrolyzed to give heptachloro-alpha-naphthoic acid.

EXAMPLE 10

The procedure outlined in Example 1 is followed except that 2,7-dicarbomethoxynaphthalene is used instead of 2,6-dicarbomethoxynaphthalene. The product is 3,4,6,8-tetrachloro-2,7-dicarbomethoxynaphthalene.

EXAMPLE 11

The procedure outlined in Example 1 is followed except that 1,8-dicarbomethoxynaphthalene is used instead of the 2,6-isomer. The product is 3,4,6,7-tetrachloro-1,8-dicarbomethoxynaphthalene.

EXAMPLE 12

The procedure outlined in Example 1 is followed except that 2,3-dicarbomethoxynaphthalene is used instead of 2,6-dicarbomethoxynaphthalene. The product is 4,5,6,8-tetrachloro-2,3-dicarbomethoxynaphthalene.

EXAMPLE 13

To a 500 milliliter stirred reactor are added 25 parts of alpha-methyl naphthoate, 400 parts of tetrachloroethylene, 1 part metallic iron and 1 part ferric chloride. The reaction mixture is brought to reflux and chlorinated for 6.5 hours by bubbling molecular chlorine through the reaction mixture. The solvent is removed by steam distillation and the residue distilled at 2 mm pressure. The product, 2,3,4,7,8-pentachloro-alpha-methyl naphthoate, boils at 190°–210°C/2 mm.

EXAMPLE 14

To a 500 milliliter stirred reactor are added 25 parts beta-methyl naphthoate, 400 parts tetrachloroethylene, 1 part metallic iron and 1 part ferric chloride. The reaction mixture is brought to reflux and chlorinated for 6 hours by bubbling molecular chlorine through the reaction mixture. The solvent is removed by steam distillation. The residue is crystallized from chloroform-hexane mixture to give 1,4,5,6,7-pentachloro-beta-methyl naphthoate.

EXAMPLE 15

In order to demonstrate the pesticidal properties of the heretofore unreported nuclearly polychlorinated compounds of the present invention, separate, sprayable solutions are made up, each solution comprising, by weight, 67.5% xylene, 7.5% Triton X-155 (an alkylaryl polyether alcohol as disclosed in U.S. Pat. No. 2,504,064), and 25% of one of the following: 1,4-dichloro-2,6-dicarbomethoxynaphthalene, 1,4,7,8-tetrachloro-2,6-dicarbomethoxynaphthalene, 1,3,4,7,8-pentachloro-2,6-dicarbomethoxynaphthalene, hexachloro-2,6-dicarbomethoxynaphthalene, 3,4,5,7-tetrachloro-alpha-methyl naphthoate, 2,4,5,6,8-pentachloro-alpha-methyl naphthoate, 2,3,4,6,7,8-hexachloro-alpha-methyl naphthoate, 1,3,4,7,8-pentachloro-beta-methyl naphthoate, and heptachloro-alpha-naphthalene carbonyl chloride. The solutions are applied to the seed leaves of bean plants to determine their effectiveness against the Mexican bean beetle. Insect mortality is observed to range from 65% to 75% after exposure for three days. Similar results are obtained when the solutions are tested for their effectiveness against the boll weevil, codling moth and red spider. Pesticidally effective dusting compositions can be made with the nuclearly polychlorinated compounds of this invention utilizing such materials as Attaclay, diatomaceous earth, soil, and the like.

What is claimed is:
1. 1,4-dichloro-2,6-dicarbomethoxynaphthalene.
2. 1,4,7,8-tetrachloro-2,6-dicarbomethoxy-naphthalene.
3. 1,3,4,7,8-pentachloro-2,6-dicarbomethoxy-naphthalene.
4. Hexachloro-2,6-dicarbomethoxynaphthalene.
5. 3,4,5,7-tetrachloro-alpha-methyl naphthoate.
6. 2,4,5,6,8-pentachloro-alpha-methyl naphthoate.
7. 2,3,4,6,7,8-hexachloro-alpha-methyl naphthoate.
8. 1,3,4,7,8-pentachloro-beta-methyl naphthoate.

* * * * *